United States Patent [19]

Pitha

[11] Patent Number: 4,649,040
[45] Date of Patent: Mar. 10, 1987

[54] THERAPY FOR RETINOID PATHOGENESIS
[75] Inventor: Josef Pitha, Baltimore, Md.
[73] Assignee: The United States of America as represented by the Department of Health and Human Services, Washington, D.C.
[21] Appl. No.: 607,160
[22] Filed: May 4, 1984
[51] Int. Cl.⁴ .................. A61K 31/095; A61K 31/195
[52] U.S. Cl. ..................................... 424/10; 514/562; 514/706
[58] Field of Search .................... 424/10; 514/706, 562

[56] References Cited
PUBLICATIONS

The Merck Index, Entry 5845, (1976).
CA 67:18251a, "The Influence of Testosterone on the Induction of Fatty Liver by Methionine Deficiency 1967.
CA 73:12119r, Myoimositol V. Effect of Myoinositol on the Prevention of Fatty Liver Induced by Orotic Acid; 1970.
CA75:4398g, "Toxicological Assessment of Choline Chloride & Lipotrophic Effect" 1970.
77:15050e Effects of Long Term Alcohol Administration on the Development of Fatty Cirrhosis in Choline Defecient Rats 1972.
101:71476z Ameliorating Effects of Carnitine and its Precursors on Alcohol Induced Fatty Liver 1984.
Peck, Retinoids Therapeutic Use in Dermatology Drugs 24:341-351 (1982).
CA: 91;55094t Effect of Vitamin A on Nitrogen Metabolism in Mineral Substances, histo Structure of the Thyroid Gland of Young Rams 1977.
CA 71:21052z, Vitamin Enriched Grains Fr 1,530,248 6/1968.
CA 73:74385h, Influence of Vitamin A on the Development of Young Swine with Varying Levels of Complete Protein in Ration 1969.
CA 68:38349n Mushrooms in Foods 1966.
CA 74:21136s Effect of Glucocorticoid, Vitamin A, and Estrogens on Human Fetal Skin in Organ Culture.

Primary Examiner—Stanley J. Friedman
Attorney, Agent, or Firm—Holman & Stern

[57] ABSTRACT

The present invention discloses a pharmaceutical composition and a method of treating retinoid induced pathogenesis. The pathological effect of retinoid is ameliorated by a suitable dose of a rescuing agent selected from the group consisting of choline chloride, methionine, betaine, biotin and inositol, the rescuing agent having the property of preventing formation of fatty liver.

5 Claims, 2 Drawing Figures

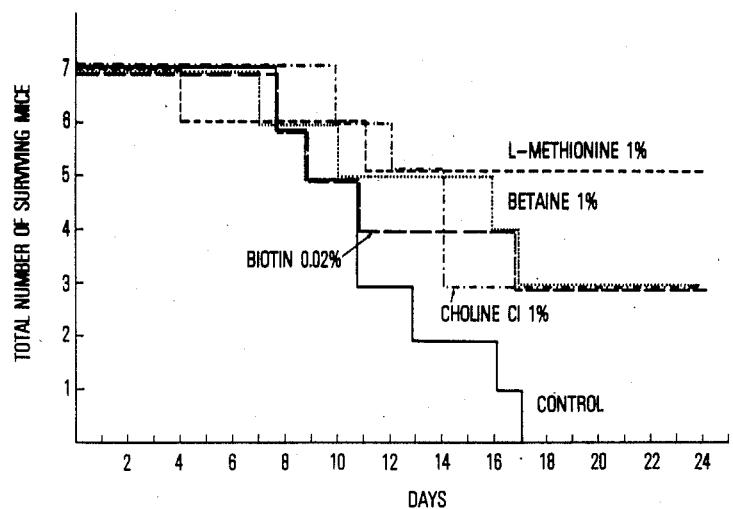
FIG. 1  SURVIVAL OF MICE POISONED BY 13-TRANS RETINOIC ACID:
EFFECTS OF RESCUING AGENTS
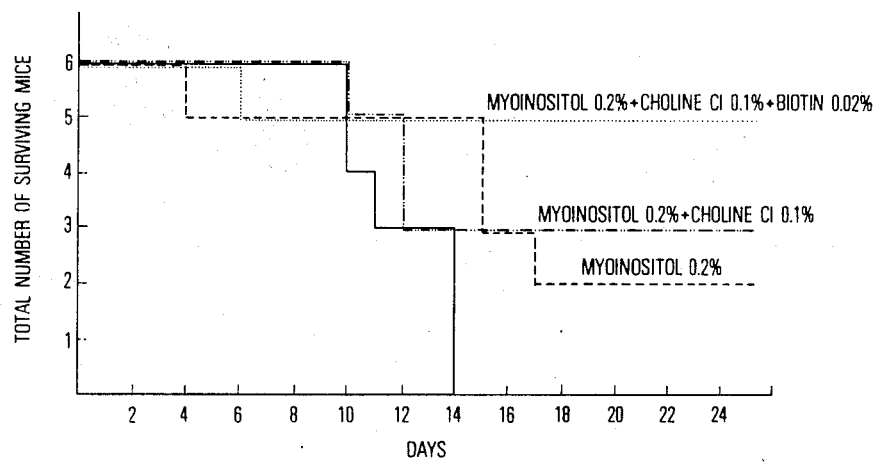
FIG. 2  SURVIVAL OF MICE POISONED BY 13-TRANS RETINOIC ACID:
EFFECTS OF MIXTURES OF RESCUING AGENTS

THERAPY FOR RETINOID PATHOGENESIS

BACKGROUND OF THE INVENTION

1. Technical Field

The present invention is related to a pharmaceutical composition and a method for treating pathological changes induced by high doses of retinoids. More particularly, the present invention is related to the use of rescuing agents for ameliorating retinoid induced pathogenesis, the rescuing agents being a group of substances which prevent formation of fatty liver.

2. Prior Art

Retinoids are lipophilic compounds possessing chemical and biological similarities to vitamin A. Retinoids mainly affect epithelial cells, both in vitro and in vivo and are critical for differentiation and maintenance of all epithelial tissues. Retinoid deficiency causes avitaminosis-A, which can be reversed by low doses of a suitable retinoid. At much higher doses, retinoids are employed for treating dermatological problems ranging from acne to psoriasis to skin cancer (Peck, Drugs 24: 341-351, 1982). In addition, retinoids have potential use in prevention of chemical carcinogenesis (Sporn, et al., Federation Proceedings 35: 1332-1338, 1976; Bolag, Cancer Chemother. Pharmacol. 3, 207-215, 1979) and in treatment of rheumatoid arthritis (Brinkerhoff, et al., Science 221, 756-758, 1983). However, at the therapeutic doses required for treating dermatological and other problems or ailments, retinoids evoke distinct pathological changes.

The pathological changes or the toxic symptoms of retinoids induced in humans are similar to those in experimental animals. Thus, in man, the symptoms of retinoid toxicity include weight loss, dry and chapping skin, dryness of the oral mucosa, facial dermatitis, conjunctivitis, and hair loss (Peck, supra). In mice high doses of retinoids were seen to cause loss of weight, skin scaling, loss of hair, and bone fracture (Bolag, Europ. J. Cancer 10: 731-737, 1974). These reports clearly demonstrate the symptomalogical similarities of retinoid pathogenesis in humans and mice.

It has been reported that although various retinoids may differ in relative bioeffectiveness, their toxic symptoms are quite similar. For example, a natural compound, 13-trans retinoic acid, and its synthetic aromatic analog, etretinate, differ in the dose required to induce pathological changes, but do not differ in the pathological changes induced (Bolag, supra). It has been suggested that the similarity of toxic effects may be based at least in part on metabolic interconversion of these compounds (McCormick, et al., Biochemistry 22: 3933-3940, 1983).

It has also been reported that different modes of application of retinoids also result in analogous toxic symptoms (Bolag and Peck, supra). Hence, it is not possible to avoid the systemic pathological effects of retinoids by changing the mode of application, e.g. by topical application rather than oral administration.

To enable better therapeutic usage of retinoids various chemically modified compounds of this class have been prepared and evaluated (Pawson, et al., J. Med. Chem. 25: 1269-1277, 1982). Currently three of these retinoids are known to be used in humans: tretinoin (13-trans-retinoic acid); isotretinoin (13-cis-retinoic acid) and etretinate (all-trans-9-(4-methoxy-2,3,3-trimethylphenyl)-3,7-dimethyl-2,4,6,8-nonatetraemoate). It has been reported that the toxic effects of 13-cis-retinoic acid can be lowered by adjusting specific dosage regimens (Peck, U.S. Pat. No. 4,322,438).

In another approach to the problem, the toxicity of several retinoids was decreased by increasing their water solubility through formation of complexes (Pitha, U.S. Pat. No. 4,371,673, Pitha, et al., Life Sciences 32: 719-723, 1983).

The Applicant has now discovered that the pathological or toxic effects of retinoids can be substantially reduced by administering a compound selected from the group consisting of agents which prevent formation of fatty liver.

SUMMARY OF THE INVENTION

It is, therefore, an object of the present invention to provide a method of treating pathological changes induced by administration of high doses of retinoids.

It is another object of the present invention to provide a pharmaceutical composition for the therapy of retinoid pathogenesis.

Other objects and advantages will become evident as the description of the invention proceeds.

DETAILED DESCRIPTION OF THE INVENTION

These and other objects, features and many of the attendant advantages of the invention will be better understood upon a reading of the following detailed description when considered in connection with the accompanying drawings wherein:

FIG. 1 shows the effect of rescuing agents on tretinoin induced poisoning in mice.

FIG. 2 shows the effect of the mixture of rescuing agents on tretinoin induced poisoning in mice.

The term retinoids include all those lipophilic compounds which possess chemical and biological similarities to vitamin A. Retinoids of particular interest are tretinoin (13-trans-retinoic acid), isotretinoin (13-cis-retinoic acid) and etretinoin (all-trans-9-(4-methoxy-2,3,3-trimethylphenyl)-3,7-dimethyl-2,4,6,8-nonatetraemoate).

In accordance with the present invention any agent or compound which prevents the formation of fatty liver can be used to ameliorate the pathological or toxic effects of retinoids. Preferred agents known to prevent formation of fatty liver include biotin, chloline chloride, methionine, betaine, inositol and the like. These agents or compounds, hereinafter termed "rescuing agents", may be used either alone, in mixture or in combination with other agents or compounds including retinoids. They may be administered in any suitable vehicle, form and mode, e.g., as tablets, capsules, solids, liquids, emulsions, ointments, paste, slurry, mixtures, solutions, suspensions, orally, subcutaneously, intraperitoneally, in sterile aqueous media or physiological saline and the like. The rescuing agents may also be administered in the form of precursors or congeners, e.g., in the form of lecithin which is the precursor of choline. Suitable carriers, fillers, additives, adjuvants, fortifiers and the like well known in the art may also be combined or admixed with these rescuing agents. Other ingredients or agents which increase the water solubility or absorption of these rescuing agents may also be employed.

PREFERRED EMBODIMENTS OF THE INVENTION

In the experiments described hereunder mice (C57 BL/6J-males) were used. A toxic dose of 13-trans retinoic acid, 500 mg/kg, was administered by an intraperitoneal injection of the suspension of the acid in physiological saline. This one time dose has several pathological effects in mice as described by Bolag, supra, and results in death of nearly all of the animals. Mice injected with retinoic acid were thereafter divided into the following groups: (a) control animals which received tap water to drink; (b) treated groups which, in place of tap water, were supplied with solutions of various rescuing agents in tap water.

The progress of the development of pathological changes were followed daily. Results of three independent experiments are shown in FIGS. 1 and 2. These results are representative of other similar tests. Experiments were also conducted which established the non-toxicity of the rescuing agents mentioned herein.

Results in FIG. 1 show that the administration of 1% (weight by volume) choline chloride or 0.02% biotin or 1% betaine in drinking water rescued about 40% of mice from death caused by retinoic acid. In the same experiment a supersaturated solution of biotin (0.06%) was also used. This led to the rescue of about 50% of the mice. The most potent substance of the group was L-methionine, which at 1% concentration led to the rescue of 70% of the mice.

FIG. 2 shows the results of addition of 0.2% of myoinositol (inositol) to drinking water which rescued about 30% of the mice from death induced by retinoic acid. The percentage of rescue increased to 50% when myoinositol was supplemented by 0.1% of choline chloride. FIG. 2 also shows the results of another experiment wherein the mixture of myoinositol and choline chloride was further supplemented with biotin (0.02%). The results clearly demonstrate that an increased rescue (about 80%) can be achieved by such a supplementation.

The experimental evidence presented herein clearly establishes that a group of agents known to prevent formation of fatty liver, when administered in sufficient doses ameliorates the pathological changes induced by retinoids. Without being bound to any theory, it is suggested that these agents presumably accelerate metabolism and excretion of retinoids thereby reducing their toxic or pathological effects. These rescuing agents are minor components of certain foods and are non-toxic. They are easily assimilable and show immediate and efficacious utility.

It is understood that the examples and embodiments described herein are for illustratie purposes only and that various modifications or changes in light thereof will be suggested to persons skilled in the art and are to be included within the spirit and purview of this application and the scope of the appended claims.

What is claimed is:

1. A pharmaceutical composition for ameliorating retinoid pathogenesis consisting essentially of a mixture selected from the group consisting of (a) about 1% by weight of L-methionine and about 1% by weight of betaine; and (b) about 0.2% by weight of myoinositol, about 0.1% by weight of choline and about 0.02% by weight of biotin; and physiologically acceptable carrier.

2. A pharmaceutical composition for ameliorating retinoid pathogenesis consisting essentially of a mixture selected from the group consisting of (a) about 1% by weight of L-methionine and about 1% by weight of betaine; and (b) about 0.2% by weight of myoinositol, about 0.1% by weight of choline and about 0.02% by weight of biotin; admixed with therapeutic amount of a retinoid and pharmaceutically acceptable carrier.

3. A pharmaceutical composition for ameliorating retinoid pathogenesis consisting essentially of a mixture selected from the group consisting of (a) about 1% by weight of L-methionine and about 1% by weight of betaine; and (b) about 0.2% by weight of myoinositol, about 0.1% by weight of choline and about 0.02% by weight of biotin; an amount of an agent which increases water solubility of said mixture and pharmaceutically acceptable carrier.

4. A method for ameliorating retinoid pathogenesis in mammals comprising administering to a mammal an amount of an agent as defined in claim 1 effective to ameliorate retinoid pathogenesis.

5. The method of claim 4 administering said agent orally.

* * * * *